United States Patent [19]

Bubert et al.

[11] Patent Number: 5,733,724
[45] Date of Patent: Mar. 31, 1998

[54] OLIGONUCLEOTIDES FOR THE DETECTION OF ENTEROBACTERIACEAE SELECTED FROM SALMOLYSIN

[75] Inventors: Andreas Bubert; Werner Goebel; Monika Goetz, all of Gerbrunn; Albrecht Ludwig, Wurzburg; Peter Schubert, Darmstadt; Siegfried Neumann, Seeheim-Jugenheim, all of Germany

[73] Assignee: Merck Patent Gesellschaft Mit Beschrankter Haftung, Darmstadt, Germany

[21] Appl. No.: 332,747

[22] Filed: Nov. 1, 1994

[30] Foreign Application Priority Data

Nov. 2, 1993 [DE] Germany .................. 43 37 295.3

[51] Int. Cl.$^6$ .................. C12Q 1/68; C12P 19/34; C07H 21/02; C07H 21/04
[52] U.S. Cl. .................. 435/6; 435/912; 536/243; 536/24.31; 536/24.32; 536/24.33
[58] Field of Search .................. 435/6, 91.2; 536/24.3, 536/24.31, 24.32, 24.33

[56] References Cited

U.S. PATENT DOCUMENTS 4,683,202  7/1987  Mullis .................. 435/91

OTHER PUBLICATIONS

Libby et al, "A cytolysin encoded by Salmonella is required for survival within macrophages", Proc. Natl. Acad. Sci. 91(2):489–493, Jan. 1994.
Libby et al, "Cloning and characterization of a cytotoxin gene from Salmonella typhimurium", Res. Microbiol. 141:775–783, 1990.
Stratagene catalog, p. 39, 1988.
"Molecular Hybridization of Immobilized Nucleic Acids: Theoretical Concepts and Practical Considerations", Wahl et al., Methods in Enzymology, vol. 152, 1987, pp. 399 through 407.
"Hybridization of DNA or RNA Immobilized on Filters to Radioactive Probes", Maniatis et al., Molecular Cloning, 1982, pp. 324–325.
"Efficient isolation of genes by using antibody probes", Young et al., Proc. Natl. Acad. Sci. (USA), vol. 80, Mar. 1983, pp. 1194–1198.
"Use of the DNA polymerase chain reaction for homology probing: Isolation of partial cDNA or genomic clones encoding the iron–sulfur protein of succinate dehydrogenase from several species", Gould et al., Proc. Natl. Acad. Sci. (USA), vol. 86, Mar. 1989, pp. 1934–1938.
"Use of synthetic oligonucleotides as hybridization probes: Isolation of clones cDNA sequences for human $\beta_2$–microglobulin*", Suggs et al., Proc. Natl. Acad. Sci., vol. 78, No. 11, Nov. 1981, pp. 6613–6617.
"Purification of $\alpha$–hemolysin from an overproducing E. coli strain", Gonzales–Carreró et al., Mol. Gen. Genet, vol. 199, 1985, pp. 106–110.

Primary Examiner—George C. Elliott
Assistant Examiner—Jeffrey Fredman
Attorney, Agent, or Firm—Millen, White, Zelano & Branigan, P.C.

[57] ABSTRACT

The invention relates to oligonucleotides which are suitable for use as nucleic acid probes or as primers for the detection of Enterobacteriaceae, in particular of pathogenic Enterobacteriaceae, such as, for example, Salmonella sp. The oligonucleotides according to the invention are selected from the salmolysin-like DNA region and possess a sequence according to one of the formulae IIIa to IIIh, or a corresponding complementary sequence:

| | | |
|---|---|---|
| GAA TAT ATT GCG TTA GAT TAA T | IIIa | (SEQ ID NO:19) |
| AAA CTG AAG CTA CAG GTG CC | IIIb | (SEQ ID NO:20) |
| CTT AGC AAG CTA ATT ATA AGG | IIIc | (SEQ ID NO:21) |
| GGC ACG GTT GGT GCG CAT TTG G | IIId | (SEQ ID NO:22) |
| GCC ATA CGT GTG GCC ATG TGA | IIIe | (SEQ ID NO:23) |
| GGC GTG TGG TCA GTA ACC TGA | IIIf | (SEQ ID NO:24) |
| TTG CTG GCC AGC ACG ACA CG | IIIg | (SEQ ID NO:25) and |
| GAA TCA TCA CCG CCC TGA AT | IIIh | (SEQ ID NO:25). |

10 Claims, No Drawings

SEQUENCE LISTING ( 1 ) GENERAL INFORMATION:

( i i i ) NUMBER OF SEQUENCES: 26

( 2 ) INFORMATION FOR SEQ ID NO: 1:

( i ) SEQUENCE CHARACTERISTICS:
        ( A ) LENGTH: 1295 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Salmonella sp.

( x i ) SEQUENCE DESCRIPTION: SEQ ID NO: 1:

```
ATCGATGCTT  TAGTTTTAGC  CAAAACTGAA  GCTACAGGTG  CCAAGTGCGC  ACTATGTCTG     60
AAAAAATGTC  TATTGGTAAG  CAAATTTAGC  AATACATTTG  TTTTGAGAAT  ACAAATACTG    120
CACACTATTC  TAAAATCAGC  ATAATAACTT  AGCAAGCTAA  TTATAAGGAG  ATGAAATTGG    180
AATCGCCACT  AGGTTCTGAT  CTGGCACGGT  TGGTGCGCAT  TTGGCGTGCT  CTGATTGACC    240
ATCGCCTCAA  GCCTCTGGAA  TTGACGCAGA  CACATTGGGT  CACGTTGCAC  AATATTCATC    300
AATTGCCGCC  TGACCAGTCG  CAGATTCAAT  TGGCTAAAGC  GATAGGCATT  GAGCAGCCAT    360
CGCTGGTACG  CACGTTGGAT  CAACTTGAAG  ATAAGGGGCT  AATTTCGCGG  CAAACCTGCG    420
CCAGCGATCG  TCGCGCTAAG  CGGATTAAAC  TGACCGAAAA  AGCGGAGCCG  CTGATCGCTG    480
AGATGGAAGA  GGTCATTCAT  AAAACGCGCG  GTGAAATTTT  GGCTGGGATT  CTTCAGAGG     540
AGATTGAGCT  TCTGATTAAA  CTTATCGCCA  AACTTGAACA  CAATATTATG  GAATTGCACT    600
CTCACGATTG  AGGTGCAGGG  GCATACGTGT  GGCCATGTGA  CCACACGTAA  AGCCTGGTTT    660
AGCGTGGAGA  GACGGTAACC  TGGCTGCCGT  TGCTGGCCAG  CACGACACGC  TGACCTGCCG    720
AGAAACGCGT  ATTTCCTTGT  TTCTGCACAA  CCATAATGGT  GTTGCCATCG  TCTTTACGAA    780
TTTCCAGTTC  CACACCCTGG  GTTTTATTCA  TTGCGCTCTG  GACGCCCTGG  CCCGCTACGC    840
```

| | | | | | |
|---|---|---|---|---|---|
| CGCCAGCCAC | CGCGCCTGCC | GCGGTCGCCA | GTGAACGACC | CGTACCGCCG | CCGATAGTGT | 900 |
| TGCCGAGGAA | TCCGCCCAAC | ACCGCGCCGC | CGATAGCGCC | AATCACGTTA | GAATCATCAC | 960 |
| CGCCCTGAAT | TTGAACCGGA | CGAACGTTAA | CGATAGTACC | GTACGTTACA | TTCTGAACTT | 1020 |
| GTTTAGCCTC | GGATGCGGTA | TAAACATCAC | CCGAAAGGCT | ATCATTGTTA | ACACACCCCG | 1080 |
| CTAGGGATAA | CCCCATCAGT | GAAACGGCCA | GTACACGTTT | AATCATTTAC | CCATCTCCTG | 1140 |
| TTCTTCACGA | AACGCTATTT | CAGCATCCCT | ATAGCTAAAT | TATATGGCAT | TTATGCAGTT | 1200 |
| AAGGTCATAT | CTTCTGCCGA | AGAATGTGA | AAATCATAAT | CAGAAGTTAA | TTAACCAATC | 1260 |
| TTAAACGAAG | TCGGAAGCAA | GAAAGATAG | GTCAT | | | 1295 |

( 2 ) INFORMATION FOR SEQ ID NO: 2:

( i ) SEQUENCE CHARACTERISTICS:
        ( A ) LENGTH: 1253 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Escherichia coli ( x i ) SEQUENCE DESCRIPTION: SEQ ID NO: 2:

| | | | | | |
|---|---|---|---|---|---|
| GAATATATTG | CGTTAGATTA | ATAAATATTC | TTTAAGTGCG | AAAAATTTAC | GCGCAATTTC | 60 |
| TGAAAAATAT | GTCTGACGGT | AACCAAATGC | AGCAATACAT | TTGTTTAGC | AATACAATTG | 120 |
| CTGCACACTA | TTCTAAAAGC | CGCATAATAT | CTTAGCAAGC | TAATTATAAG | GAGATGAAAT | 180 |
| TGGAATCGCC | ACTAGGTTCT | GATCTGGCAC | GGTTGGTGCG | CATATGGCGT | GCTCTGATAG | 240 |
| ACCATCGCCT | GAAACCGCTG | GAGTTAACAC | AAACCCATTG | GGTTACGTTA | CACAATATCC | 300 |
| ATCAGTTACC | TCCAGACCAG | TCGCAAATTC | AACTGGCAAA | GCGATTGGC | ATCGAGCAGC | 360 |
| CATCACTGGT | CCGTACTCTG | GACCAACTGG | AAGAAAAGG | GTTAATTTCG | CGTCAAACTT | 420 |
| GTGCCAGCGA | TCGTCGGGCT | AAACGTATTA | AACTGACGGA | AAAGGCAGAG | CCGCTGATCA | 480 |
| GCGAAATGGA | AGCTGTTATT | AACAAAACCC | GCGCGGAAAT | ATTACATGGC | ATCTCCGCAG | 540 |
| AGGAACTGGA | GCAACTGATT | ACGCTCATCG | CAAAACTTGA | GCATAATATC | ATTGAGTTAC | 600 |
| AGGCCAAAGG | GTGAAATGAA | GGGGGCGTGT | GGTCAGTAAC | CTGACCACAC | GCAAACTTAT | 660 |
| TTAGCGCGGA | GAAACGGTCA | CCTGACTGCC | ATTGCTGGCC | AGTACGACAC | GTTGGCCCGG | 720 |
| AGAGAAACGA | GTGTTGCCTT | GTTTCTGTAC | CACCATGATG | GTATTACCAT | CGTCTTTACG | 780 |
| AATTTCCAGC | TCGACACCCT | GCGTTTTGTT | CATTGCACTC | TGTACGCCCT | GACCAGCTAC | 840 |
| GCCACCTGCA | ACAGCGCCTG | CTGCAGTAGC | CAGAGAACGC | CCGGTTCCGC | CACCAACAGT | 900 |
| ATTCCCCAGG | AAACCACCAA | GAACAGCACC | GCCAATTGCA | CCGATAACGT | TGGAATCATC | 960 |
| ACCGCCCTGA | ATCTGTACCG | GACGTACGTT | AACGATGGTG | CCATAGCTGA | CATTCTGTAC | 1020 |
| TTGTTTCGCT | TCAGAAGCGG | TATAAACATC | CCTGACAGG | GTGTCGTTAT | TAACACAACC | 1080 |
| GACAAGAGAC | AGACCTACCA | TTGAAACAAC | CAATACGCGT | TTAATCATTG | AAAAATCTCC | 1140 |
| TGTTCACCAT | GAAACGCCAC | GCAAGCATCC | CTCATGGTCA | AAGTATATGG | CATATGTGAA | 1200 |
| TCCATGGTTA | CATGTTCTAC | CAAATATGAG | CAAATCATAA | TGAAAGTAGG | ATC | 1253 |

( 2 ) INFORMATION FOR SEQ ID NO: 3:

(i) SEQUENCE CHARACTERISTICS:
    (A) LENGTH: 16 base pairs
    (B) TYPE: nucleic acid
    (C) STRANDEDNESS: double
    (D) TOPOLOGY: linear (ii) MOLECULE TYPE: DNA (genomic)

(iii) HYPOTHETICAL: NO (iv) ANTI-SENSE: NO (v) ORIGINAL SOURCE:
    (A) ORGANISM: Escherichia coli (xi) SEQUENCE DESCRIPTION: SEQ ID NO: 3:

TATATTGCGT TAGATT                                                                       16

(2) INFORMATION FOR SEQ ID NO: 4:

(i) SEQUENCE CHARACTERISTICS:
    (A) LENGTH: 14 base pairs
    (B) TYPE: nucleic acid
    (C) STRANDEDNESS: double
    (D) TOPOLOGY: linear (ii) MOLECULE TYPE: DNA (genomic)

(iii) HYPOTHETICAL: NO (iv) ANTI-SENSE: NO (v) ORIGINAL SOURCE:
    (A) ORGANISM: Salmonella sp.

(xi) SEQUENCE DESCRIPTION: SEQ ID NO: 4:

CTGAAGCTAC AGGT                                                                         14

(2) INFORMATION FOR SEQ ID NO: 5:

(i) SEQUENCE CHARACTERISTICS:
    (A) LENGTH: 15 base pairs
    (B) TYPE: nucleic acid
    (C) STRANDEDNESS: double
    (D) TOPOLOGY: linear (ii) MOLECULE TYPE: DNA (genomic)

(iii) HYPOTHETICAL: NO (iv) ANTI-SENSE: NO (v) ORIGINAL SOURCE:
    (A) ORGANISM: Salmonella sp.

(xi) SEQUENCE DESCRIPTION: SEQ ID NO: 5:

AGCAAGCTAA TTATA                                                                        15

(2) INFORMATION FOR SEQ ID NO: 6:

(i) SEQUENCE CHARACTERISTICS:
    (A) LENGTH: 16 base pairs
    (B) TYPE: nucleic acid
    (C) STRANDEDNESS: double
    (D) TOPOLOGY: linear (ii) MOLECULE TYPE: DNA (genomic)

(iii) HYPOTHETICAL: NO (iv) ANTI-SENSE: NO (v) ORIGINAL SOURCE:

(A) ORGANISM: Salmonella sp.

(xi) SEQUENCE DESCRIPTION: SEQ ID NO: 6:

ACGGTTGGTG CGCATT                                                                                                    16

(2) INFORMATION FOR SEQ ID NO: 7:

(i) SEQUENCE CHARACTERISTICS:
      (A) LENGTH: 15 base pairs
      (B) TYPE: nucleic acid
      (C) STRANDEDNESS: double
      (D) TOPOLOGY: linear (ii) MOLECULE TYPE: DNA (genomic)

(iii) HYPOTHETICAL: NO (iv) ANTI-SENSE: NO (vi) ORIGINAL SOURCE:
      (A) ORGANISM: Salmonella sp.

(xi) SEQUENCE DESCRIPTION: SEQ ID NO: 7:

ATACGTGTGG CCATG                                                                                                     15

(2) INFORMATION FOR SEQ ID NO: 8:

(i) SEQUENCE CHARACTERISTICS:
      (A) LENGTH: 15 base pairs
      (B) TYPE: nucleic acid
      (C) STRANDEDNESS: double
      (D) TOPOLOGY: linear (ii) MOLECULE TYPE: DNA (genomic)

(iii) HYPOTHETICAL: NO (iv) ANTI-SENSE: NO (vi) ORIGINAL SOURCE:
      (A) ORGANISM: Escherichia coli (xi) SEQUENCE DESCRIPTION: SEQ ID NO: 8:

GTGTGGTCAG TAACC                                                                                                     15

(2) INFORMATION FOR SEQ ID NO: 9:

(i) SEQUENCE CHARACTERISTICS:
      (A) LENGTH: 14 base pairs
      (B) TYPE: nucleic acid
      (C) STRANDEDNESS: double
      (D) TOPOLOGY: linear (ii) MOLECULE TYPE: DNA (genomic)

(iii) HYPOTHETICAL: NO (iv) ANTI-SENSE: NO (vi) ORIGINAL SOURCE:
      (A) ORGANISM: Salmonella sp.

(xi) SEQUENCE DESCRIPTION: SEQ ID NO: 9:

CTGGCCAGCA CGAC                                                                                                      14

(2) INFORMATION FOR SEQ ID NO: 10:

(i) SEQUENCE CHARACTERISTICS:
      (A) LENGTH: 14 base pairs
      (B) TYPE: nucleic acid
      (C) STRANDEDNESS: double
      (D) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
    ( A ) ORGANISM: Salmonella sp.

( x i ) SEQUENCE DESCRIPTION: SEQ ID NO: 10:

TCATCACCGC CCTG                                                                          14

( 2 ) INFORMATION FOR SEQ ID NO: 11:

( i ) SEQUENCE CHARACTERISTICS:
        ( A ) LENGTH: 16 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Escherichia coli ( i x ) FEATURE:
        ( A ) NAME/KEY: misc_feature
        ( B ) LOCATION:1
        ( D ) OTHER INFORMATION:/number=1
            / note= "0-20 ADDITIONAL NUCLEOTIDES"

( i x ) FEATURE:
        ( A ) NAME/KEY: misc_feature
        ( B ) LOCATION:16
        ( D ) OTHER INFORMATION:/number=2
            / note= "0-20 ADDITIONAL NUCLEOTIDES"

( x i ) SEQUENCE DESCRIPTION: SEQ ID NO: 11:

TATATTGCGT TAGATT                                                                 16

( 2 ) INFORMATION FOR SEQ ID NO: 12:

( i ) SEQUENCE CHARACTERISTICS:
        ( A ) LENGTH: 14 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Salmonella sp.

( i x ) FEATURE:
        ( A ) NAME/KEY: misc_feature
        ( B ) LOCATION:1
        ( D ) OTHER INFORMATION:/number=1
            / note= "0-20 ADDITIONAL NUCLEOTIDES"

( i x ) FEATURE:
        ( A ) NAME/KEY: misc_feature
        ( B ) LOCATION:14
        ( D ) OTHER INFORMATION:/number=2
            / note= "0 - 20 ADDITIONAL NUCLEOTIDES"

( x i ) SEQUENCE DESCRIPTION: SEQ ID NO: 12:

CTGAAGCTAC AGGT                                                                                              14

(2) INFORMATION FOR SEQ ID NO: 13:

(i) SEQUENCE CHARACTERISTICS:
        (A) LENGTH: 15 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Salmonella sp.

(ix) FEATURE:
        (A) NAME/KEY: misc_feature
        (B) LOCATION:1
        (D) OTHER INFORMATION:/number=1
            / note= "0 - 20 ADDITIONAL NUCLEOTIDES"

(ix) FEATURE:
        (A) NAME/KEY: misc_feature
        (B) LOCATION:15
        (D) OTHER INFORMATION:/number=2
            / note= "0 - 20 ADDITIONAL NUCLEOTIDES"

(xi) SEQUENCE DESCRIPTION: SEQ ID NO: 13:

AGCAAGCTAA TTATA                                                                                             15

(2) INFORMATION FOR SEQ ID NO: 14:

(i) SEQUENCE CHARACTERISTICS:
        (A) LENGTH: 16 base pairs
        (B) TYPE: nucleic acid
        (C) STRANDEDNESS: double
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Salmonella sp.

(ix) FEATURE:
        (A) NAME/KEY: misc_feature
        (B) LOCATION:1
        (D) OTHER INFORMATION:/number=1
            / note= "0 - 20 ADDITIONAL NUCLEOTIDES"

(ix) FEATURE:
        (A) NAME/KEY: misc_feature
        (B) LOCATION:16
        (D) OTHER INFORMATION:/number=2
            / note= "0 - 20 ADDITIONAL NUCLEOTIDES"

(xi) SEQUENCE DESCRIPTION: SEQ ID NO: 14:

ACGGTTGGTG CGCATT                                                                                            16

(2) INFORMATION FOR SEQ ID NO: 15:

(i) SEQUENCE CHARACTERISTICS:
        (A) LENGTH: 15 base pairs
        (B) TYPE: nucleic acid
        (C) STRANDEDNESS: double
        (D) TOPOLOGY: linear (ii) MOLECULE TYPE: DNA (genomic)

(i i i) HYPOTHETICAL: NO (i v) ANTI-SENSE: NO (v i) ORIGINAL SOURCE:
    (A) ORGANISM: Salmonella sp.

(i x) FEATURE:
    (A) NAME/KEY: misc_feature
    (B) LOCATION:1
    (D) OTHER INFORMATION:/number=1
        / note= "0 - 20 ADDITIONAL NUCLEOTIDES"

(i x) FEATURE:
    (A) NAME/KEY: misc_feature
    (B) LOCATION:15
    (D) OTHER INFORMATION:/number=2
        / note= "0 - 20 ADDITIONAL NUCLEOTIDES"

(x i) SEQUENCE DESCRIPTION: SEQ ID NO: 15:

ATACGTGTGG CCATG    15

(2) INFORMATION FOR SEQ ID NO: 16:

(i) SEQUENCE CHARACTERISTICS:
        (A) LENGTH: 15 base pairs
        (B) TYPE: nucleic acid
        (C) STRANDEDNESS: double
        (D) TOPOLOGY: linear (i i) MOLECULE TYPE: DNA (genomic)

(i i i) HYPOTHETICAL: NO (i v) ANTI-SENSE: NO (v i) ORIGINAL SOURCE:
        (A) ORGANISM: Escherichia coli (i x) FEATURE:
        (A) NAME/KEY: misc_feature
        (B) LOCATION:1
        (D) OTHER INFORMATION:/number=1
            / note= "0 - 20 ADDITIONAL NUCLEOTIDES"

(i x) FEATURE:
        (A) NAME/KEY: misc_feature
        (B) LOCATION:15
        (D) OTHER INFORMATION:/number=2
            / note= "0 - 20 ADDITIONAL NUCLEOTIDES"

(x i) SEQUENCE DESCRIPTION: SEQ ID NO: 16:

GTGTGGTCAG TAACC    15

(2) INFORMATION FOR SEQ ID NO: 17:

(i) SEQUENCE CHARACTERISTICS:
        (A) LENGTH: 14 base pairs
        (B) TYPE: nucleic acid
        (C) STRANDEDNESS: double
        (D) TOPOLOGY: linear (i i) MOLECULE TYPE: DNA (genomic)

(i i i) HYPOTHETICAL: NO (i v) ANTI-SENSE: NO (v i) ORIGINAL SOURCE:
        (A) ORGANISM: Salmonella sp.

(i x) FEATURE:
        (A) NAME/KEY: misc_feature
        (B) LOCATION:1
        (D) OTHER INFORMATION:/number=1

-continued

/ note= "0 - 20 ADDITIONAL NUCLEOTIDES"

( i x ) FEATURE:
    ( A ) NAME/KEY: misc_feature
    ( B ) LOCATION:14
    ( D ) OTHER INFORMATION:/number=2
        / note= "0 - 20 ADDITIONAL NUCLEOTIDES"

( x i ) SEQUENCE DESCRIPTION: SEQ ID NO: 17:

CTGGCCAGCA CGAC                                  14

( 2 ) INFORMATION FOR SEQ ID NO: 18:

( i ) SEQUENCE CHARACTERISTICS:
        ( A ) LENGTH: 14 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Salmonella sp.

( i x ) FEATURE:
        ( A ) NAME/KEY: misc_feature
        ( B ) LOCATION:1
        ( D ) OTHER INFORMATION:/number=1
            / note= "0 - 20 ADDITIONAL NUCLEOTIDES"

( i x ) FEATURE:
        ( A ) NAME/KEY: misc_feature
        ( B ) LOCATION:14
        ( D ) OTHER INFORMATION:/number=2
            / note= "0 - 20 ADDITIONAL NUCLEOTIDES"

( x i ) SEQUENCE DESCRIPTION: SEQ ID NO: 18:

TCATCACCGC CCTG                                  14

( 2 ) INFORMATION FOR SEQ ID NO: 19:

( i ) SEQUENCE CHARACTERISTICS:
        ( A ) LENGTH: 22 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Escherichia coli ( x i ) SEQUENCE DESCRIPTION: SEQ ID NO: 19:

GAATATATTG CGTTAGATTA AT                         22

( 2 ) INFORMATION FOR SEQ ID NO: 20:

( i ) SEQUENCE CHARACTERISTICS:
        ( A ) LENGTH: 20 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
  ( A ) ORGANISM: Salmonella sp.

( x i ) SEQUENCE DESCRIPTION: SEQ ID NO: 20:

AAACTGAAGC TACAGGTGCC   20

( 2 ) INFORMATION FOR SEQ ID NO: 21:

( i ) SEQUENCE CHARACTERISTICS:
  ( A ) LENGTH: 21 base pairs
  ( B ) TYPE: nucleic acid
  ( C ) STRANDEDNESS: double
  ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
  ( A ) ORGANISM: Salmonella sp.

( x i ) SEQUENCE DESCRIPTION: SEQ ID NO: 21:

CTTAGCAAGC TAATTATAAG G   21

( 2 ) INFORMATION FOR SEQ ID NO: 22:

( i ) SEQUENCE CHARACTERISTICS:
  ( A ) LENGTH: 22 base pairs
  ( B ) TYPE: nucleic acid
  ( C ) STRANDEDNESS: double
  ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
  ( A ) ORGANISM: Salmonella sp.

( x i ) SEQUENCE DESCRIPTION: SEQ ID NO: 22:

GGCACGGTTG GTGCGCATTT GG   22

( 2 ) INFORMATION FOR SEQ ID NO: 23:

( i ) SEQUENCE CHARACTERISTICS:
  ( A ) LENGTH: 21 base pairs
  ( B ) TYPE: nucleic acid
  ( C ) STRANDEDNESS: double
  ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
  ( A ) ORGANISM: Salmonella sp.

( x i ) SEQUENCE DESCRIPTION: SEQ ID NO: 23:

GGCATACGTG TGGCCATGTG A   21

( 2 ) INFORMATION FOR SEQ ID NO: 24:

( i ) SEQUENCE CHARACTERISTICS:

```
            ( A ) LENGTH: 21 base pairs
            ( B ) TYPE: nucleic acid
            ( C ) STRANDEDNESS: double
            ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
            ( A ) ORGANISM: Escherichia coli ( x i ) SEQUENCE DESCRIPTION: SEQ ID NO: 24:

GGCGTGTGGT CAGTAACCTG A                                                          21

( 2 ) INFORMATION FOR SEQ ID NO: 25:

( i ) SEQUENCE CHARACTERISTICS:
            ( A ) LENGTH: 20 base pairs
            ( B ) TYPE: nucleic acid
            ( C ) STRANDEDNESS: double
            ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
            ( A ) ORGANISM: Salmonella sp.

( x i ) SEQUENCE DESCRIPTION: SEQ ID NO: 25:

TTGCTGGCCA GCACGACACG                                                            20

( 2 ) INFORMATION FOR SEQ ID NO: 26:

( i ) SEQUENCE CHARACTERISTICS:
            ( A ) LENGTH: 20 base pairs
            ( B ) TYPE: nucleic acid
            ( C ) STRANDEDNESS: double
            ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
            ( A ) ORGANISM: Salmonella sp.

( x i ) SEQUENCE DESCRIPTION: SEQ ID NO: 26:

GAATCATCAC CGCCCTGAAT                                                            20
```

OLIGONUCLEOTIDES FOR THE DETECTION OF ENTEROBACTERIACEAE SELECTED FROM SALMOLYSIN

BACKGROUND OF THE INVENTION

The invention relates to oligonucleotides which are suitable, as nucleic acid probes or as primers, for detecting Enterobacteriaceae, in particular pathogenic Enterobacteriaceae, such as, for example, Salmonella sp.

*Escherichia coli*, Salmonella sp. and Shigella sp. are those representatives of the Enterobacteriaceae family which most frequently cause food poisoning. There has recently been an increase in cases of food poisoning, especially those caused by salmonellas; this has involved a rise both in the frequency and in the severity of the outbreaks.

Rapid and specific methods for detecting salmonellas and other pathogenic Enterobacteriaceae represent a prerequisite for the rapid and specific treatment of infected patients and for the speedy containment of the source of the infection. Statutory regulations require that the methods for detecting salmonellas must be sensitive for these bacteria irrespective of pathogenicity and virulence. Customary methods for detecting salmonellas comprise multi-step culture and serological typing. Several days elapse before the results achievable by these methods are available. While immunological methods are more rapid, they can only be used insofar as it can be guaranteed that the marker employed is always being expressed; this inevitably results in these methods suffering from limitations. These limitations do not apply to detection methods which are based on the use of nucleic acid probes. However, detection using nucleic acid probes is generally not sufficiently sensitive for it to be possible to dispense with a preliminary culture. For this reason, the colony-hybridization method represents a common variant.

Detection methods which are based on nucleic-acid amplification reactions, for example, the polymerase chain reaction (PCR), improve the limit of detection so that a preliminary culture can generally be dispensed with.

Methods for detecting salmonellas based on the polymerase chain reaction are known from the literature:

a) Spierungs et al., Gene, 122:45–52 (1992), employed primers from the phoE gene of *S. typhimurium*. However, not all the strains of the genus Salmonella that were examined were recognized in the detection reaction.

b) Rahn et al., Molecular and Cellular Probes, 6:271–279 (1992), employed primers from the invA gene. However, not all the strains of the genus Salmonella that were examined were recognized in the detection reaction; PCR products also appeared in controlled experiments with other Enterobacteriaceae.

EP-A-0 355 989 and EP-A-0 383 509 disclose methods for detecting salmonellas using nucleic acid probes. The sequences which are detected here are, respectively, from the araC gene and from a gene which encodes a particular group of fimbriae.

Because the detection of salmonellas requires an extremely high degree of diagnostic sensitivity, there still remains, therefore, the object of providing improved detection methods which are based on the nucleic-acid probe technique and/or on nucleic-acid amplification reactions.

SUMMARY OF THE INVENTION

It has been found that a group of genes which are responsible for expressing hemolytic toxins in pathogenic *E. coli* strains are also present in other Enterobacteriaceae. This finding was surprising since many of the strains examined do not form any hemolytic toxins but nevertheless possess these genes.

Upon further study of the specification and appended claims, further objects and advantages of this invention will become apparent to those skilled in the art.

Two of these genes were discovered for the first time in salmonellas which form hemolytic toxins and named slyA and slyC. It was found that constituent sequences selected from the slyA and slyC gene regions are suitable for use in specific detection methods. These detection methods according to the invention can be based on the nucleic-acid probe technique and/or other on nucleic-acid amplification reactions; they make it possible to detect bacteria of the genus Salmonella and/or other Enterobacteriaceae with a high degree of specificity.

The definition "a salmolysin DNA region" is understood to mean, according to the invention, the DNA regions which comprise, in the genus Salmonella, the coding segments (slyA and slyC), including their flanking non-coding regions, which are necessary for the function of salmolysin. The "salmolysin-like DNA regions" are understood to mean the DNA regions which comprise these segments in bacteria of the genus Salmonella and in other Enterobacteriaceae.

The invention relates to oligonucleotides, selected from the salmolysin-like DNA region, for the detection of Enterobacteriaceae, characterized in that they contain a constituent sequence according to one of the formulae Ia to Ih or an affiliated complementary sequence, it being possible for up to 20 additional nucleotide building blocks to be present in bonded form upstream and/or downstream of the particular constituent sequence:

| | |
|---|---|
| TAT ATT GCG TTA GAT T | Ia (SEQ ID NO:3) |
| CTG AAG CTA CAG GT | Ib (SEQ ID NO:4) |
| AGC AAG CTA ATT ATA | Ic (SEQ ID NO:5) |
| ACG GTT GGT GCG CAT T | Id (SEQ ID NO:6) |
| ATA CGT GTG GCC ATG | Ie (SEQ ID NO:7) |
| GTG TGG TCA GTA ACC | If (SEQ ID NO:8) |
| CTG GCC AGC ACG AC | Ig (SEQ ID NO:9) |
| TCA TCA CCG CCC TG | Ih (SEQ ID NO:10) |

In this context, oligonucleotides are particularly preferred which have a sequence according to one of the formulae IIIa to IIIh or have an affiliated complementary sequence:

| | |
|---|---|
| GAA TAT ATT GCG TTA GAT TAA T | IIIa (SEQ ID NO:19) |
| AAA CTG AAG CTA CAG GTG CC | IIIb (SEQ ID NO:20) |
| CTT AGC AAG CTA ATT ATA AGG | IIIc (SEQ ID NO:21) |
| GGC ACG GTT GGT GCG CAT TTG G | IIId (SEQ ID NO:22) |
| GGC ATA CGT GTG GCC ATG TGA | IIIe (SEQ ID NO:23) |
| GGC GTG TGG TCA GTA ACC TGA | IIIf (SEQ ID NO:24) |
| TTG CTG GCC AGC ACG ACA CG | IIIg (SEQ ID NO:25) |
| GAA TCA TCA CCG CCC TGA AT | IIIh (SEQ ID NO:26) |

The invention relates to the use of an oligonucleotide according to one of the formulae IIa–h and/or IIIa–h as a nucleic acid probe or as a primer for the detection of Enterobacteriaceae, in particular of bacteria of the genus Salmonella.

The invention relates to methods for the detection of Enterobacteriaceae, in particular of bacteria of the genus Salmonella, characterized in that an oligonucleotide according to one of the formulae IIa–h and/or IIIa–h is used as a nucleic acid probe or as a primer.

The invention relates to test compilations or kits for the detection of Enterobacteriaceae, in particular of bacteria of the genus Salmonella, characterized in that the compilations contain an oligonucleotide according to one of the formulae IIa–h and/or IIIa–h as a nucleic acid probe or as a primer.

SEQ ID NO. 1 depicts the sequence of the DNA region which encodes salmolysin gene products in bacteria of the genus Salmonella; and SEQ ID NO. 2 depicts the sequence of the corresponding DNA region in *E. coli*. The region of the sequence from position 1 to 972 in *Shigella flexneri* is homologous to that in *E. coli*.

DETAILED DESCRIPTION

The invention is described in more detail below. In this context, chemical, immunological and molecular biological methods which are known to the person skilled in the art, and the particulars of which are described in the literature, are not as a rule entered into in detail. Use can also be made of variants of these methods, which variants are known per se but not described in detail in this present publication.

It is known to the person skilled in the art that the replacement of one, or of a few, bases in a nucleotide sequence frequently does not alter the biological properties of this sequence. Thus, it is known that two nucleic acid segments can still hybridize when individual bases do not correspond precisely to the complementary structure. For this reason, the nucleotide sequences according to the invention also comprise those which are derived by base exchange from the sequences IIa–IIh and IIIa–IIIh and which hybridize in the same way as the respective original sequence.

Suitable hybridization conditions for the use of the DNA sequences of the present invention in the claimed methods are routinely determinable by one of ordinary skill in the art, e.g., as outlined in Sambrook et al., Molecular Cloning, 2d ed. (1989), or Innis et al. (eds.), PCR Protocols (Academic Press, Inc., Harcourt Brace Jovanovich, Publishers). Thus, for example, for the use of the primers of this invention for the PCR reaction, the primer binding step can be carried out at standard or high stringency conditions, e.g., with primer pair Salm5/Entro3-2 under high stringency conditions (58° C. annealing temperature) and with primer pair Salm5/Salm3-1 under standard stringency conditions (55° C. annealing temperature). When the nucleic acids to be detected by hybridization are the products of PCR reactions, where the sequences of the products to be detected are known exactly, high stringency conditions, e.g., hybridization at 48° C. overnight, (1) washing step in 5×SSC, 0.5% SDS at 37° C. for 30 min., (2+3) washing step in 0.5×SSC, 0.5% SDS at 65° for 15 min. (according to the reference Biotechnics, 10(1):94–101 (1991)) can be employed. When the DNA probes are used for other detection methods, e.g., colony hybridization, at least the first screening can be conducted under low stringency conditions, e.g., 30°–37° C. If necessary, secondary screening of positives can be conducted under higher stringency conditions, e.g., 37°–42° C., e.g., using two or more replicate tests with different probes to confirm the test. Methods of optimization of these hybridization conditions, in order to reduce both false negatives and false positive results, are well known to the skilled worker.

Depending on the particular sequence, the oligonucleotides according to the invention may be synthesized by methods which are known to the person skilled in the art, for example, the phosphotriester method or the phosphoamidite method. The phosphoamidite method is preferably employed, in particular using automated synthesizers. The method is described in Tetrahedron Lett., 22:1859–1862 (1981). Further details of synthesis methods of this type are given, for example, in Winnacker, Gene und Klone (Genes and Clones), pp. 44–61 (1985) (VCH-Verlagsgesellschaft mbH, Weinheim).

The oligonucleotides according to the invention of the formulae IIa–IIh and IIIa–IIIh are suitable to be used as nucleic acid probes and consequently to be used for the specific detection of Enterobacteriaceae, in particular of bacteria of the genus Salmonella. Their sequences are presented in the customary manner, being written from the 5' end to the 3' end. Since nucleic acid probes hybridize with a target sequence and since for every target sequence there is always a complementary sequence on the opposite strand, oligonucleotides which possess a sequence complementary to one of the formulae IIa–h or IIIa–h are also, in the same way, suitable for use in accordance with the invention.

Nucleic acid probes are customarily bound to tracers in order to permit analytical detection. For example, the probes themselves can be labelled radioactively with $^{32}P$ or $^{3}H$. The method for labelling with isotopes, and other radioisotopes which are suitable for the labelling, are known to the person skilled in the art. The person skilled in the art is familiar with other, non-isotopic tracers in addition to these radioactive tracers. These non-isotopic tracers are frequently preferred for analytical purposes. These labels are bonded to the probe, for example, using bridging molecules. Examples of suitable non-isotopic tracers are fluorescent substances, such as, for example, fluorescein, or also enzymes, such as, for example, peroxidase or alkaline phosphatase. The person skilled in the art is familiar with the choice of suitable fluorescent substances or of enzymes and with the necessary detection methods. In many cases, it is useful not to bind the tracer directly to the probe but, instead, to bind it indirectly by means of additional, strongly binding ligands. The combinations biotin/avidin or biotin/streptavidin have proved to be especially useful for this purpose. The person skilled in the art is familiar with the choice of such ligands and with the necessary binding methods. In accordance with the invention, in correspondence with these examples, the term tracers is understood to mean both the tracers employed in direct labelling methods and the combinations, including the binding ligands, employed in indirect labelling methods. In accordance with the invention, the term "nucleic acid probe" is understood to mean both the nucleic acid employed as probe and the compound consisting of nucleic acid and tracer.

The oligonucleotides according to the invention of the formulae IIa–IIh and IIIa–IIIh are also suitable to be used as primers for nucleic-acid amplification methods and consequently to be used for the specific detection of Enterobacteriaceae, in particular of bacteria of the genus Salmonella; in these methods, a preliminary culture is not generally necessary. Depending on the requirements of the amplification system which is used in each case, either deoxyribonucleotides or ribonucleotides are employed together with the sequences according to the invention. In the latter case, the thymidine building blocks are in each case replaced by uridine building blocks. Since, customarily, in each case one primer is to react with in each case one of the DNA strands, one of the primers is employed in the complementary sequence. The complementary sequence is derived in a known manner in accordance with the rules of base pairing.

The primers according to the invention can suitably be employed for DNA amplification, for example, using the polymerase chain reaction (PCR). For this purpose, the DNA is first disassociated by heating into the single strands. Two primers are used which in each case hybridize with the homologous DNA segment on, in each case, one DNA strand. The genome segment which lies between these two primers is amplified. The primers annealed to the DNA represent the starting points for the amplification. A polymerase, preferably Taq DNA polymerase, then completes the second strand, corresponding to the sequence of the original DNA, in the presence of the four nucleotide triphosphates. The resulting double strands are then once again disassociated by heating into the single strands. This amplification cycle can be repeated many times. After a sufficient number of amplification cycles, the amplified nucleic acid can be detected using known methods. To do this, the DNA can be fractionated by electrophoresis, then stained with ethidium bromide and finally detected by fluorescence using UV excitation. Detection can also be achieved by means of DNA hybridization. The details of suitable amplification and detection methods are described in review articles, for example, Innis et al., supra. Other nucleic-acid amplification methods in which the primers according to the invention can be employed are also known from the literature. These methods include the ligase chain reaction, described by Bond et al. (1990), pages 425–434 in Raven Press (New York, N.Y.).

The choice of one of the two primers is always particularly critical, whereas the second primer can be more easily varied without significantly altering the specificity of the detection reaction. Consequently, in accordance with the teaching of the present invention, it is also entirely possible for a sequence for this second primer to be chosen which does not conform to one of the formulae IIa–IIh or IIIa–IIIh.

According to the invention, at least one of the primers is selected from the formulae IIa–IIh or, preferably, from the formulae IIIa–IIIh. As has already been explained, the second primer has substantially less effect on the specificity of the amplification reaction than does the first primer. However, combinations are preferred in which both primers are selected from the formulae IIa–IIh or IIIa–IIIh.

Further information on the details of the PCR method are to be found in the previously mentioned publications of Spierungs et al. (1992) and Rahn et al. (1992).

It is also possible to detect the amplification products by nucleic acid hybridization. To do this, nucleic acid probes which hybridize with the amplified segment are added to the reaction mixture after the amplification.

Details of the preparation of the oligonucleotides according to the invention, and of their use, are apparent from the following examples. The person skilled in the art will infer additional methodological details from the cited literature. The examples are intended to explain the subject matter of the invention and do not represent any limitation of the invention.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosure of all applications, patents and publications, cited above and below, and of corresponding German application P 43 37 295.3, filed Nov. 2, 1993, are hereby incorporated by reference.

EXAMPLES

Example 1

Preparation of the Oligonucleotide in Accordance with Formula IIIb

The oligonucleotide according to formula IIIb is prepared by the phosphoamidite method using an Applied Biosystems 380A DNA synthesizer. The main features of the method are described in Tetrahedron Lett., 22:1859–1862 (1981 ). Further details are to be found in the documentation supplied by the apparatus manufacturer.

The oligonucleotides according to formulae IIIa, IIIc and IIId are prepared in a corresponding manner. The oligonucleotides according to formulae IIIf, IIIg and IIIh are prepared in the respective complementary sequence. The oligonucleotide according to formula IIIe is prepared both in the given sequence and also in the affiliated complementary sequence.

The oligonucleotides obtained in this way may be used either as DNA probes or as primers for the PCR reaction.

Example 2

Labelling a DNA Probe with $^{32}$P

An oligonucleotide obtained in accordance with Example 1 is labelled radioactively as described in paragraph 4.8 of "Current Protocols in Molecular Biology" (1988); Wiley and Sons, New York:

20 µl of a solution of gamma-$^{32}$P ATP (200 µCi), 2.5 µl of a ten times concentrated kinase buffer (0.7M Tris HCl; pH 7.5; 0.1M MgCl$_2$; 50 mM dithiothreitol, 1 mM spermidine HCl; 1 mM EDTA) and 4 units of T4 polynucleotide kinase (from Pharmacia) are added to 1 µl of oligonucleotide solution containing 100 ng of oligonucleotide, and the mixture is incubated at 37° C. for 30 minutes. The enzyme is then inactivated by heating (65° C.; 5 minutes). The labelled oligonucleotide is precipitated by the addition of 25 µl of 4M ammonium acetate solution and 250 µl of absolute ethanol, and centrifuged (15 minutes; 12,000 rpm). The sediment is suspended three times in 2.5 µl of water in each case and recentrifuged.

Example 3

Hybridization with a Radioactively Labelled DNA Probe (Colony-hybridization Method)

The colony-hybridization method is carried out in accordance with the instructions of Datta et al., Appl. and Environmental Microbiol., 54:2933–2937 (1988):

a) Pretreatment

Bacteria from the sample under investigation are precultivated on a Petri dish (brain heart infusion; 37° C.; 18 hours). A membrane filter (Hybond-C; from Amersham) is then laid on the surface of the agar on which the precultivated bacteria are present and pressed down gently. The filter is laid, with the bacteria facing upward, onto a filter paper (Whatman 3M) which is located in a plastic Petri dish containing 3 ml of NaCl solution (0.85%; w/w), and is treated for 30 seconds at 700 W in a microwave oven. Subsequently, the filter is treated, at room temperature for 5 minutes, with 3 ml of lysis solution (0.5M NaOH, 1.5M NaCl) and then briefly laid on a filter paper soaked with neutralization solution (1M Tris HCl; pH 7.0; 2M NaCl); the filter is then incubated for 5 minutes in neutralization solution and dried in air.

b) Prehybridization

The DNA which is attached to the membrane filter is prehybridized with 100 µg/ml of denatured herring sperm DNA at 45° C. for four hours in hybridization buffer of the following composition: 0.6M Tris HCl, pH 8.0, 6M NaCl and 60 mM EDTA (six times concentrated STE solution), 0.1% Ficoll®, 0.1% polyvinylpyrrolidone and 0.1% bovine serum albumin (five times concentrated Denhardt's solution), 0.1% sodium dodecyl sulfate, and also 100 µg/ml denatured herring sperm DNA.

c) Hybridization

For the hybridization, the radioactively labelled oligonucleotide probe according to formula IIIe, prepared in accordance with Example 1, is added, together with the hybridization buffer to the membrane filter containing the attached DNA. The hybridization is carried out at 45° C. over 18 hours. The filter is then washed: three times at room temperature, for 5 minutes in each case, with 0.1% sodium dodecyl sulfate in twice-concentrated SSC solution (0.3M NaCl in 30 mM trisodium citrate; pH 7.0), three times at 45° C., for 20 minutes in each case, in 0.1% sodium dodecyl sulfate in SSC solution, and once at room temperature in SSC solution.

Subsequently, the filter is laid on an X-ray film (Fuji RX medical X-ray film, from Fuji Photo Film Co.), and the film is exposed overnight. After having been developed, the black coloration indicates salmonella colonies.

Example 4

Implementation of the PCR Reaction for the Genus-specific Detection of Salmonella A sample containing bacteria, and comprising approximately 1 µg of DNA, is suspended in 50 µl of buffer (10 mM Tris HCl, pH 8.5; 1.5 mM $MgCl_2$ and 50 mM KCl) and heated at 110° C. for 5 minutes. Primers according to formulae IIIb and IIIh (see Example 1; 0.4 µg in each case), 2.5 U of Taq polymerase (from Pharmacia), dissolved in reaction buffer (10 mM Tris HCl, pH 8.5; 1.5 mM $MgCl_2$ and 50 mM KCl), and 200 µM each of dGTP, dATP, dTTP and dCTP are subsequently added (total reaction volume, 100 µl). The first denaturation step is for 3 minutes at 94° C. The sample is then temperature-equilibrated for 30 seconds at 55° C. (binding phase) and for one minute at 72° C. (elongation phase). The subsequent denaturation steps (at 94° C.) last for 45 seconds. A concluding elongation step (at 72° C.) of 5 minutes duration is carried out after 30 reaction cycles.

The PCR products are fractionated on a polyacrylamide gel (6%) in a Tris/borate (in each case 50 mM) running buffer containing EDTA (2.5 mM). The fractionated PCR products are subsequently visualized by staining with ethidium bromide (0.1 mg/ml in water) and irradiating with UV light (260 nm).

PCR products are only observed when Salmonella DNA or Salmonella cells are present in the sample (see column a) in Table 1).

Example 5

Implementation of the PCR Reaction for the Genus-specific Detection of Salmonella The method described in Example 4 is repeated using the primers according to formulae IIIe and IIIh (see Example 1) instead of the primers according to formulae IIIb and IIIh. In this case, too, PCR products are only observed when Salmonella DNA or Salmonella cells are present in the sample (see column b) in Table 1).

Example 6

Implementation of the PCR Reaction for the Genus-specific Detection of Salmonella The method described in Example 4 is repeated using the primers according to formulae IIIb and IIIe (complementary sequence) (see Example 1) instead of the primers according to formulae IIIb and IIIh. In this case, too, PCR products are only observed when Salmonella DNA or Salmonella cells are present in the sample.

Example 7

Implementation of the PCR Reaction for the Group-specific Detection of the Enterobacteriaceae Salmonella, Citrobacter, E. coli and Shigella A sample containing bacteria, and comprising approximately 1 µg of DNA, is suspended in 50 µl of buffer (10 mM Tris HCl, pH 8.5; 1.5 mM $MgCl_2$ and 50 mM KCl), and heated at 110° C. for 5 minutes.

Primers according to formulae IIIc and IIIh (see Example 1; 0.4 µg in each case), 2.5 U of Taq polymerase (from Pharmacia), dissolved in reaction buffer (10 mM Tris HCl, pH 8.5; 1.5 mM $MgCl_2$ and 50 mM KCl), and 200 µM each of dGTP, dATP, dTTP and dCTP, are subsequently added (total reaction volume, 100 µl). The first denaturation step is for 3 minutes at 94° C. The sample is then temperature-equilibrated at 55° C. for 30 seconds (binding phase) and at 72° C. for one minute (elongation phase). The subsequent denaturation steps (at 94° C.) last 45 seconds. A concluding elongation step (at 72° C.) of 5 minutes duration is carried out after 30 reaction cycles.

The PCR products are fractionated on a polyacrylamide gel (6%) in a Tris/borate (50 mM in each case) running buffer containing EDTA (2.5 mM). The fractionated PCR products are subsequently visualized by staining with ethidium bromide (0.1 mg/ml in water) and irradiating with UV light (260 nm).

PCR products are only observed when DNA or cells from the Enterobacteriaceae Salmonella, Citrobacter, E. coli or Shigella are present in the sample (see column c) in Table 1).

Example 8

Implementation of the PCR Reaction for the Group-specific Detection of the Enterobacteriaceae Salmonella, Citrobacter, E. coli and Shigella The method described in Example 7 is repeated using the primers according to formulae IIId and IIIh (see Example 1) instead of the primers according to formulae IIIc and IIIh. In this case, too, PCR products are only observed when DNA or cells from the Enterobacteriaceae Salmonella, Citrobacter, E. coli or Shigella are present in the sample (see column d) in Table 1).

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

TABLE 1

|  | a) | b) | c) | d) |
| --- | --- | --- | --- | --- |
| Primer 1 | IIIb | IIIe | IIIc | IIId |
| Primer 2 (complementary sequence) | IIIh | IIIh | IIIh | IIIh |
| Bacterial strain *Salmonella* | | | | |
| arizonae | + | + | + | + |
| choleraesuis | + | + | + | + |
| enteritidis | + | + | + | + |
| infantis | + | + | + | + |
| paratyphi A | + | + | + | + |
| paratyphi B | + | + | + | + |
| typhi | + | + | + | + |
| typhimurium | + | + | + | + |
| bovis morbificans | + | + | + | + |
| brandenburg | + | + | + | + |
| bredeney | + | + | + | + |
| derby | + | + | + | + |
| heidelberg | + | + | + | + |
| london | + | + | + | + |
| montevideo | + | + | + | + |
| saintpaul | + | + | + | + |
| senftenberg | + | + | + | + |
| thomson | + | + | + | + |
| eimsbüttel | + | + | + | + |
| *Citrobacter diversus* | — | — | + | + |
| *Escherichia coli* | — | — | + | + |

TABLE 1-continued

| | a) | b) | c) | d) |
|---|---|---|---|---|
| Shigella | | | | |
| flexneri | — | — | + | + |
| sonnei | — | — | + | + |
| Yersinia | — | — | — | — |
| Edwardsiella | — | — | — | — |
| Enterobacter aerogenes | — | — | — | — |
| Haemophilus influenzae | — | — | — | — |
| Hafnia alvei | — | — | — | — |
| Klebsiella pneumoniae | — | — | — | — |
| Neisseria meningitidis | — | — | — | — |
| Serratia | — | — | — | — |
| Pasteurella multocida | — | — | — | — |
| Proteus | — | — | — | — |
| mirabilis | — | — | — | — |
| vulgaris | — | — | — | — |

TABLE 1-continued

| | a) | b) | c) | d) |
|---|---|---|---|---|
| Pseudomonas aeruginosa | — | — | — | — |
| Vibrio parahaemolyticus | — | — | — | — |

What is claimed is:

1. An isolated oligonucleotide for the detection of Enterobacteriaceae, consisting of a sequence selected from the group consisting of formulae IIa to IIh or a sequence complementary thereto:

$X^1$ TAT ATT GCG TTA GAT T $X^2$ IIa (SEQ ID NO:11),
$X^1$ CTG AAG CTA CAG GT $X^2$ IIb (SEQ ID NO:12),
$X^1$ AGC AAG CTA ATT ATA $X^2$ IIc (SEQ ID NO:13),
$X^1$ ACG GTT GGT GCG CAT T $X^2$ IId (SEQ ID NO:14),
$X^1$ ATA CGT GTG GCC ATG $X^2$ IIe (SEQ ID NO:15),
$X^1$ GTG TGG TCA GTA ACC $X^2$ IIf (SEQ ID NO:16),
$X^1$ CTG GCC AGC ACG AC $X^2$ IIg (SEQ ID NO:17), and
$X^1$ TCA TCA CCG CCC TG $X^2$ IIh (SEQ ID NO:18), wherein $X^1$ and $X^2$, each independently, are hydrogen or 1–20 additional nucleotides.

2. An isolated oligonucleotide consisting of a sequence selected from the group consisting of formulae IIIa to IIIh, or a sequence complementary thereto:

GAA TAT ATT GCG TTA GAT TAA T IIIa (SEQ ID NO:19),
AAA CTG AAG CTA CAG GTG CC IIIb (SEQ ID NO:20),
CTT AGC AAG CTA ATT ATA AGG IIIc (SEQ ID NO:21),
GGC ACG GTT GGT GCG CAT TTG G IIId (SEQ ID NO:22),

GCC ATA CGT GTG GCC ATG TGA IIIe (SEQ ID NO:23),

GGC GTG TGG TCA GTA ACC TGA IIIf (SEQ ID NO:24),

TTG CTG GCC AGC ACG ACA CG IIIg (SEQ ID NO:25), and

GAA TCA TCA CCG CCC TGA AT IIIh (SEQ ID NO:26).

3. A method of detecting the presence of Enterobacteriaceae in a sample, comprising hybridizing the sample with an oligonucleotide of claim 1 and detecting the presence of any resulting specific hybrid, whereby the presence of a specific hybrid indicates the presence of Enterobacteriaceae in the sample.

4. A method of claim 3, wherein the oligonucleotide is a nucleic acid probe.

5. A method of claim 3, wherein the oligonucleotide is a primer for nucleic acid amplification.

6. A method of claim 3, wherein the Enterobacteriaceae is Salmonella.

7. A kit for the detection of Enterobacteriaceae in a sample, comprising a first component which is an oligonucleotide of claim 1, wherein said oligonucleotide is a nucleic acid probe or a primer, and at least one additional component selected from the group consisting of a) a hybridization reagent, b) a primer elongation reagent, c) a positive control sample, d) a negative control sample and e) a detection reagent.

8. A kit of claim 7, wherein the detection is effected using a nucleic acid probe.

9. A kit of claim 7, wherein the detection is effected by means of nucleic acid amplification, and the oligonucleotide is a primer.

10. A kit of claim 7, wherein the Enterobacteriaceae is of the genus Salmonella.

* * * * *